United States Patent
Pietschmann et al.

(10) Patent No.: US 11,602,135 B2
(45) Date of Patent: Mar. 14, 2023

(54) REPRESSORS OF VIRAL INFECTION

(71) Applicant: TWINCORE ZENTRUM FÜR EXPERIMENTELLE UND KLINISCHE INFEKTIONSFORSCHUNG GMBH, Hannover (DE)

(72) Inventors: Thomas Pietschmann, Hannover (DE); Richard Brown, Hannover (DE)

(73) Assignee: TWINCORE ZENTRUM FÜR EXPERIMENTELLE UND KLINISCHE INFEKTIONSFORSCHUNG GMBH, Hannover (DE)

( * ) Notice: Subject to any disclaimer, the term of this patent is extended or adjusted under 35 U.S.C. 154(b) by 528 days.

(21) Appl. No.: 16/306,273

(22) PCT Filed: Jun. 1, 2017

(86) PCT No.: PCT/EP2017/063378
§ 371 (c)(1),
(2) Date: Nov. 30, 2018

(87) PCT Pub. No.: WO2017/207725
PCT Pub. Date: Dec. 7, 2017

(65) Prior Publication Data
US 2019/0297860 A1  Oct. 3, 2019

(30) Foreign Application Priority Data
Jun. 2, 2016 (EP) .................................. 16172701

(51) Int. Cl.
| | | |
|---|---|---|
| *C07K 14/18* | (2006.01) | |
| *C12N 15/10* | (2006.01) | |
| *C12N 15/11* | (2006.01) | |
| *G01N 33/00* | (2006.01) | |
| *A01K 67/027* | (2006.01) | |
| *A61P 31/14* | (2006.01) | |
| *A61K 48/00* | (2006.01) | |
| *C07K 14/705* | (2006.01) | |
| *C12N 15/113* | (2010.01) | |
| *G01N 33/50* | (2006.01) | |
| *C07K 14/00* | (2006.01) | |
| *A61K 38/00* | (2006.01) | |

(52) U.S. Cl.
CPC ...... *A01K 67/0278* (2013.01); *A01K 67/0276* (2013.01); *A61K 48/0066* (2013.01); *A61P 31/14* (2018.01); *C07K 14/00* (2013.01); *C07K 14/705* (2013.01); *C07K 14/7056* (2013.01); *C12N 15/113* (2013.01); *G01N 33/5091* (2013.01); *A01K 2217/052* (2013.01); *A01K 2217/054* (2013.01); *A01K 2217/058* (2013.01); *A01K 2217/072* (2013.01); *A01K 2217/075* (2013.01); *A01K 2267/0337* (2013.01); *A61K 38/00* (2013.01); *C12N 2310/14* (2013.01); *C12N 2770/24211* (2013.01)

(58) Field of Classification Search
None
See application file for complete search history.

(56) References Cited

U.S. PATENT DOCUMENTS 9,510,570 B2 * 12/2016 Tang ..................... A01K 67/02
2015/0113673 A1   4/2015 Tang et al.

FOREIGN PATENT DOCUMENTS

| WO | 2010040001 A1 | 4/2010 |
| WO | 2015073319 A1 | 5/2015 |

OTHER PUBLICATIONS

Brown et al., Liver-expressed Cd302 and Cr1I limit hepatitis C virus cross-species transmission to mice (Sci Adv, 2020, 6:1-18) (Year: 2020).*
Lo et al. Characterization of the Expression and Function of the C-Type Lectin Receptor CD302 in Mice and Humans Reveals a Role in Dendritic Cell Migration (J. Immun, 2016; 197:885-89) (Year: 2016).*
Xu et al., A Critical Role for Murine Complement Regulator Crry in Fetomaternal Tolerance (Science, 2000, 287:498-501) (Year: 2000).*
Rubattu et al., Ndufc2 Gene Inhibition Is Associated With Mitochondrial Dysfunction and Increased Stroke Susceptibility in an Animal Model of Complex Human Disease (J Am Heart Ass, 2016, 5:1-5) (Year: 2016).*
Gamp et al., LIMP-2/LGP85 deficiency causes ureteric pelvic junction obstruction, deafness and peripheral neuropathy in mice (Human Mol Genetics, 2003, 12:631-646) (Year: 2003).*
Kozaki et al., Role of zinc-finger anti-viral protein in host defense against Sindbis virus (Int Immu, 2015, 27:357-364) (Year: 2015).*
Watashi et al., NTCP and Beyond: Opening the Door to Unveil Hepatitis B Virus Entry. Int. J. Mol. Sci. 2014, 15, 2892-2905 (Year: 2014).*
Chockalingam, K., et al., "A cell protection screen reveals potent inhibitors of multiple stages of the hepatitis C virus life." PNAS, Feb. 2010, 107(8): 3764-3769.

(Continued)

Primary Examiner — Arthur S Leonard
(74) Attorney, Agent, or Firm — Saliwanchik, Lloyd & Eisenschenk

(57) ABSTRACT

The present invention pertains to a non-human genetically modified animal with increased susceptibility to infection with a human virus. The invention suggests to genetically impair the expression of newly identified viral infection repression factors CD302, Cr1I, Ndufc2, AW112010, Scarb2 and Zc3hav1, which markedly improves infection with human viruses in none-human hosts. Furthermore provided are methods for the generation of the animal of the invention, methods for increasing or reducing the susceptibility of a cell to viral infection, methods for screening novel modulators of viral infection as well as new therapy options for the treatment of viral diseases, in particular hepatitis C.

11 Claims, 13 Drawing Sheets

(56) References Cited

OTHER PUBLICATIONS

Hart, D.N.J., et al., "Functional Studies on the C-Type Lectin Receptor CD302 Present on Dendritic Cells and Macrophages." Blood, 2015, 126: 2198.

Mailly, L., et al., "Hepatitis C virus infection and related liver disease: the quest for the best animal model." Frontiers in Microbiology, Jul. 2013, 4(212): 1-11.

Masciopinto, F., et al., "Expression of Human CD81 in Transgenic Mice Does Not Confer Susceptibility to Hepatitis C virus Infection." Virology, 2002, 304: 187-196.

Yamayoshi, S., et al., "Receptors for enterovirus 71." Emerging Microbes and Infections, 2014, 3: e53; doi:10,1038/emi.2014.49, pp. 1-7.

Berggren, Keith A. et al. "Animal Models Used in Hepatitis C Virus Research," International Journal of Molecular Sciences, vol. 21, 20 pages, published in 2020.

Vercauteren, Koen et al. "HCV animal models and liver disease," Journal of Hepatology, vol. 61, pp. S26-S33, 2014.

\* cited by examiner

Figure 1:
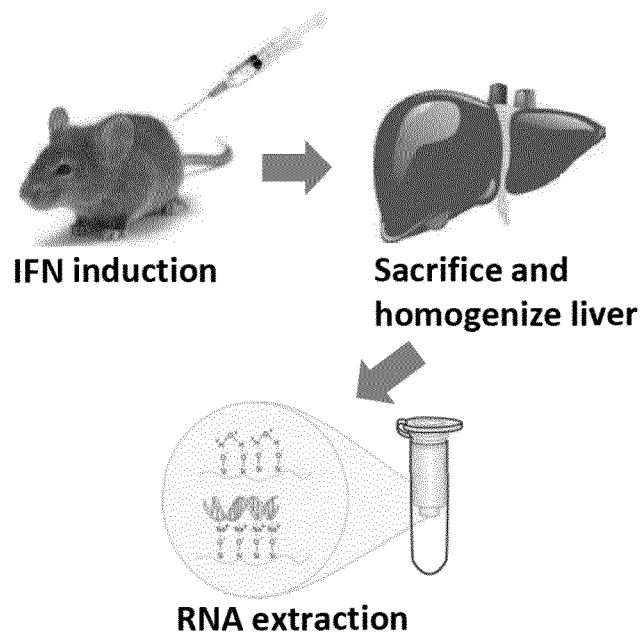
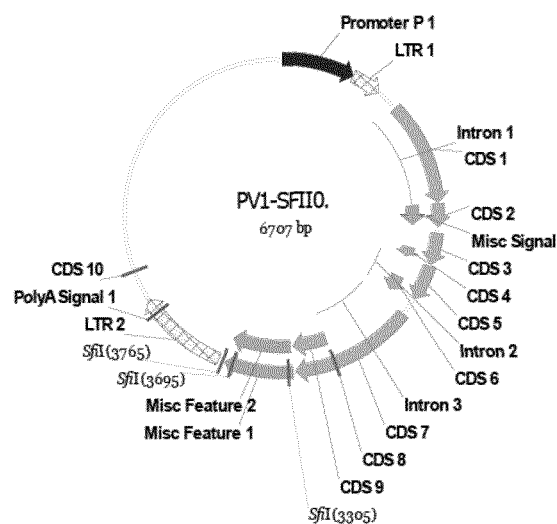

Figure 2:
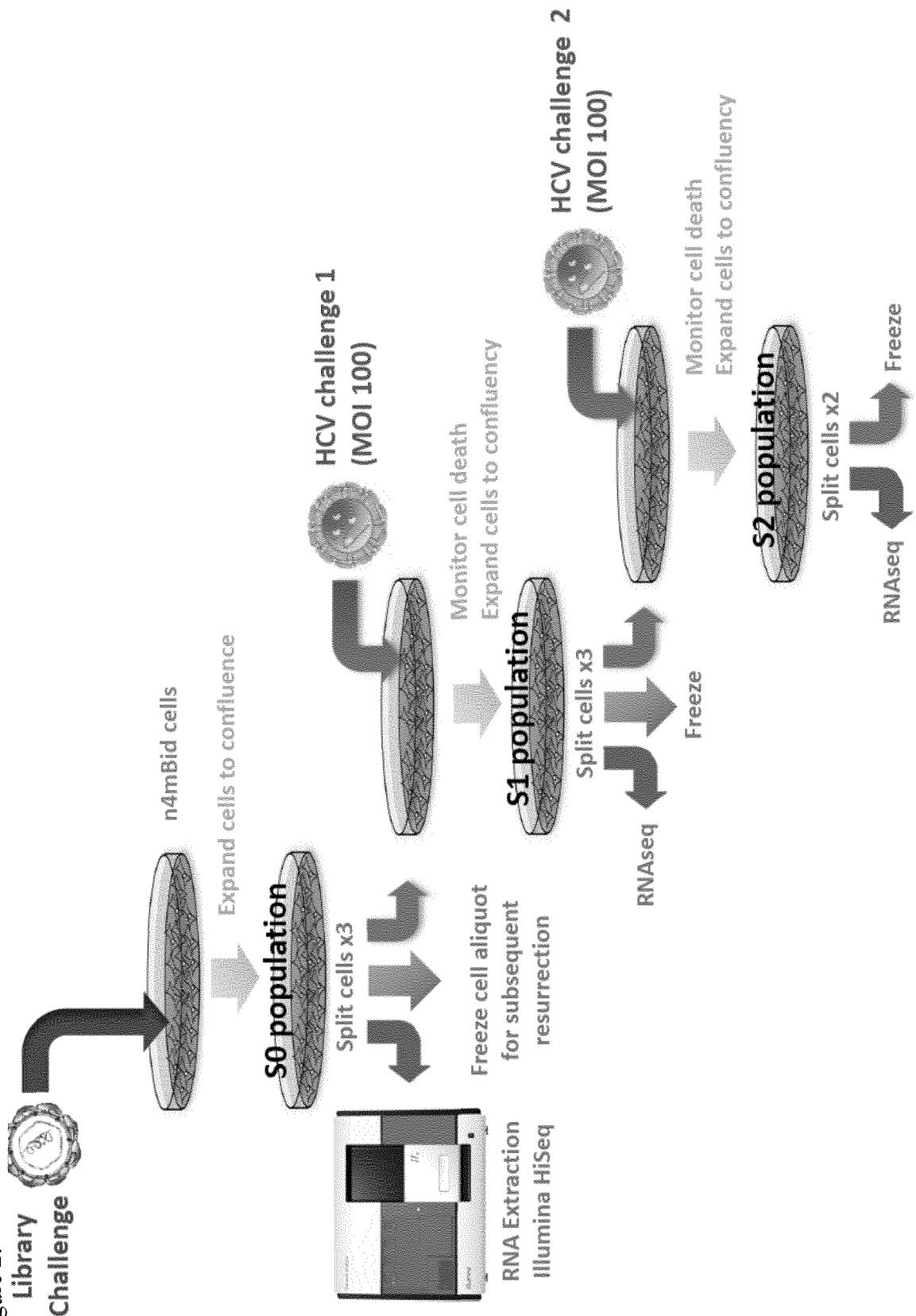

Figure 2: Library Challenge

Figure 4:
A:
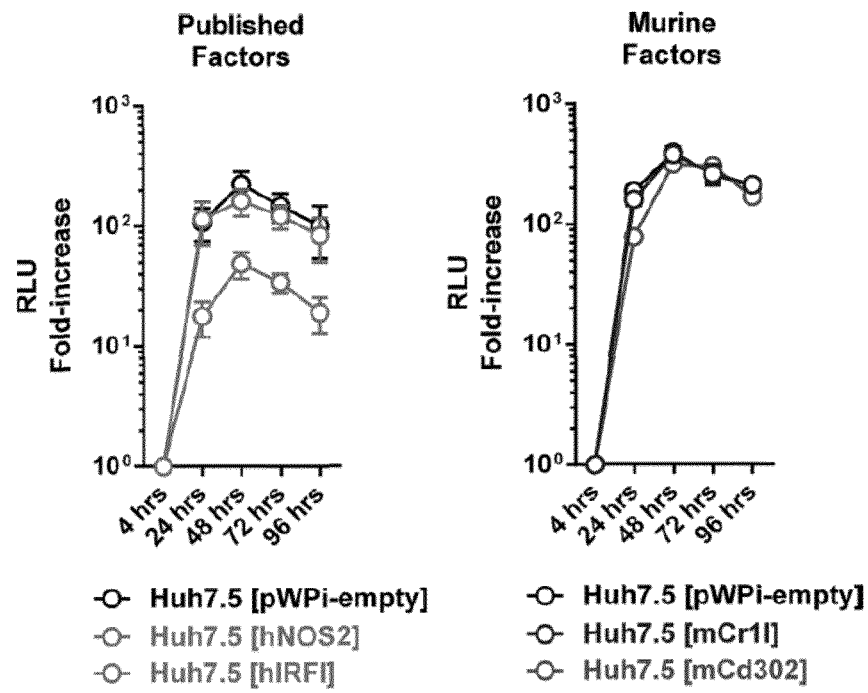
B:
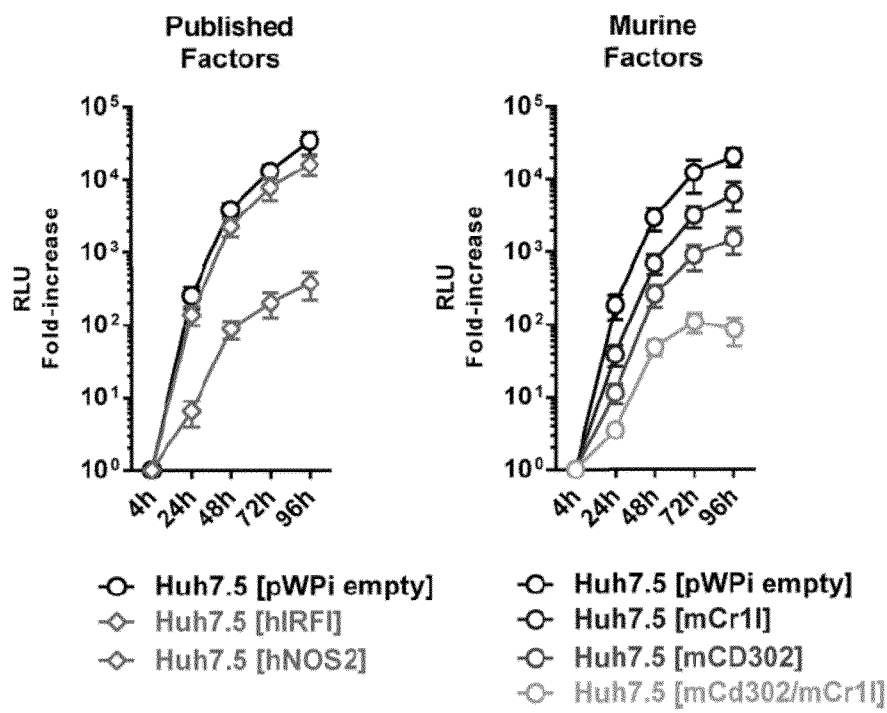

A:

B:

Figure 9:
A:
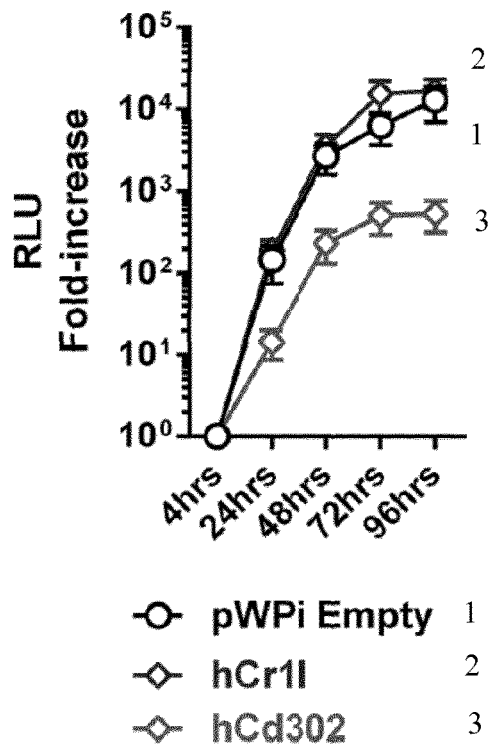
B:
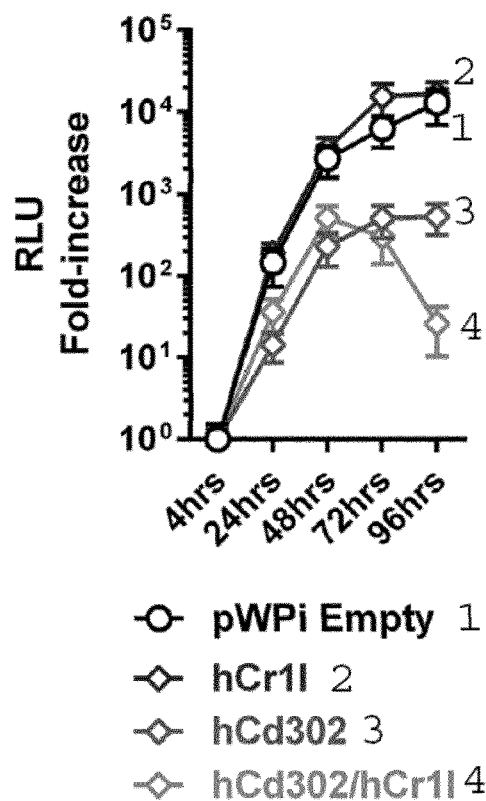

REPRESSORS OF VIRAL INFECTION

CROSS REFERENCE TO RELATED APPLICATIONS

This application is a National Stage Application of International Application Number PCT/EP2017/063378, filed Jun. 1, 2017; which claims priority to European Patent Application No. 16172701.1, filed Jun. 2, 2016.

FIELD OF THE INVENTION

The present invention pertains to a non-human genetically modified animal with increased susceptibility to infection with a human virus. The invention suggests to genetically disrupt the expression of newly identified viral infection repression factors CD302, Cr1l, Ndufc2, AW112010, Scarb2 and/or Zc3hav1, which markedly improves infection with human viruses in none-human hosts. Furthermore provided are methods for the generation of the animal of the invention, methods for increasing or reducing the susceptibility of a cell to viral infection, methods for screening novel modulators of viral infection as well as new therapy options for the treatment of viral diseases, in particular hepatitis C.

DESCRIPTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection are based on combination therapies including directly acting antivirals targeting the viral protease NS3/4A, the NS5A phosphoprotein, and/or the viral RNA dependent RNA polymerase NS5B. However, these therapies are very expensive thus limiting access to therapy particularly in resource-poor countries where HCV prevalence is highest. Moreover, there is no established vaccine for HCV. Consequently, there is an urgent need for improved therapeutic agents that effectively combat chronic HCV infection and for development of a prophylactic vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The non-structural (NS) proteins are believed to provide the catalytic machinery for viral replication. The NS3/4A protease releases NS5B, the RNA-dependent RNA polymerase from the poly-protein chain. HCV NS5B polymerase is required for the synthesis of a double-stranded RNA from a single-stranded viral RNA that serves as a template in the replication cycle of HCV.

The understanding of viral infection and virus life cycle is still uncomplete. Unfortunately, until today only limited small animal models exist for studying hepatitis viral infection—a major drawback for the development of vaccines. The determinants restricting HCV tropism to human and chimpanzee hosts are incompletely understood. Replication of the viral RNA has been demonstrated in mouse cells, but these cells are not infectable with either lentiviral particles bearing HCV glycoproteins (HCVpp) or HCV produced in cell culture (HCVcc) (unpublished data), suggesting a block at the level of entry.

WO 2010/040001 identified human Occludin (OCLN) and CD81 as essential Hepatitis C Virus (HCV) cell entry factors in human cells. Transgenic expressed occludin is shown to render murine and other non-human cells infectable with HCV and to support HCV-susceptibility of human cells. However, infection rates in vivo in a mouse model using OCLN and CD81 are very low, and still insufficient to provide a small animal model for hepatitis.

In a further approach Dorner et al. (Nature 2013) suggested a transgenic mouse expressing OCLN and CD81, while concomitantly inhibiting essential factors of the mouse endogenous antiviral response, such as STAT1, IRF1, IFN-αβR and IRF7. The downside of this approach is that the removal of the interferon system also reduces adaptive immune responses, which are necessary to perform vaccination studies in a mouse model of hepatitis.

It was therefore an object of the present invention to provide a novel strategy to create a small animal model for hepatitis infection. In this context, the invention seeks to provide novel factors that are responsible for repressing viral infection in non-human hosts.

The above problem is solved in a first aspect by a genetically modified animal whose genome comprises at least one genetic modification (mutation) compared to a wild-type genome of said animal, characterized in that the at least one genetic modification reduces the expression, function or stability of one or more proteins selected from the group consisting of CD302, Cr1l, Ndufc2, AW112010, Scarb2 and Zc3hav1.

The genetically modified animal of the invention is characterized by an increased susceptibility to a virus infection. In context of the herein disclosed invention the proteins CD302, Cr1l, Ndufc2, AW112010, Scarb2 and Zc3hav1 were identified as strong inhibitors of HCV cell entry in the mouse liver. Since many viruses gain host cell access using similar processes, the identified factors of the present invention are generally useful as repressors for viral cell entry. The genetic repression of the factors of CD302, Cr1l, Ndufc2, AW112010, Scarb2 and Zc3hav1 in the genome of a small animal therefore renders the animal susceptible for viral infections. It will be understood that the invention seeks to repress the endogenous versions of the restriction factors of the invention (CD302, Cr1l, Ndufc2, AW112010, Scarb2 and Zc3hav1) in an animal of choice. Most preferred is a mouse, and accordingly, the repression of one or more proteins of mCD302, mNdufc2, mAW112010, mCr1l, mScarb2 and mZc3HAV1 in the genome of the mouse to obtain the genetically modified animal according to the invention.

In preferred embodiments the genetically modified animal of the invention is homozygous, homozygous-null, heterozygous or hemizygous for the at least one genetic modification.

The term "endogenous" in the context of a nucleic acid or protein refers to a nucleic acid sequence or segment or to an amino acid sequence or segment that is normally found in a host organism or host cell.

The herein used gene designations refer to the murine versions of the genes as identified in the screen of the present invention. However, the invention may also be practiced in non-human animals other than mice. The person of skill understands that in this case the endogenous homologs of the recited murine genes in the respective non-human animal are meant by the recited gene names, although in practice such genes may have a different gene name. Using for example the GeneBank database the skilled artisan may easily identify the respective homologs of the mouse repression factors of the invention in other non-human animal species.

The term "increased susceptibility to infection" or similar expressions as used in the present disclosure shall be understood to mean that an alteration of any kind (genetic, therapeutic etc) of a subject as suggested by the present invention compared to a control subject that did not underwent the same alteration, results in a higher infection-rate, viral replication, viral entry or exit, and/or viral load in said subject or in a cell, organ or tissue of the subject upon infection with a virus. The increased susceptibility to infection may be due an altered process in any stage in a viral life cycle, for example an increased entry-rate of the virus into the subject or due to an increased rate of viral replication in the subject. In context of the present invention it is preferred that the "increased susceptibility to infection" is an increased rate of entry of a virus into a host cell.

In some embodiments the genetically modified animal of the invention has a reduced expression, function or stability of only one protein selected from the group consisting of CD302, Cr11, Ndufc2, AW112010, Scarb2 and Zc3hav1. In other embodiments genetically modified animals are preferred having a reduced expression, function or stability of more than one protein selected from the group consisting of CD302, Cr11, Ndufc2, AW112010, Scarb2 and Zc3hav1. For example, the following combinations are preferred: CD302 and Cr11, or of CD302 and AW112010, or of Cr11 and AW112010, or of CD302, AW112010, and Cr11. Also further combinations are possible, for example the above double/triple combinations each together with Scarb2, or together with Ndufc2, or together with Zc3hav1. Any specific and single combination possible between the herein disclosed six preferred restriction factors forms part of the herein disclosed invention.

In context of the present invention the herein disclosed factors CD302, Cr11, Ndufc2, AW112010, Scarb2 and Zc3hav1 are also often referred to as "repression factors" or "repression proteins" due to the herein firstly disclosed function as repressors of viral entry in mammalian cells. These proteins are considered as a preferred smaller group of repression proteins of the invention. Further repression factors that are used for the present invention shall include any of the other identified proteins of the screen of the invention (see examples). Therefore, the group of repression proteins in some embodiments of the invention is an enhanced group and includes the following proteins: Lgals1, Cfi, Mrps33, Cbp2, Lap4ma, 1110054M08Rik, Mterf4, SerpinC1, Gas5, Htatip2, Scarb2, Mb12, Cr11, AW112010, CD302, Zc3HAV1 and Ndufc2.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence. If the expression of the protein is recited in context of the invention, it is meant that the respective gene sequence encoding said protein is expressed to produce said protein.

As used herein the term "stability" when referring to proteins of the invention refers to an art-recognized measure of the maintenance of one or more physical properties of a protein in a cell or extracellular composition. In one embodiment, the physical property is the maintenance of the covalent structure of the protein (e.g. the absence of proteolytic cleavage, unwanted oxidation or deamidation). In another embodiment, the physical property is the presence of the protein in a properly folded state (e.g. the absence of soluble or insoluble aggregates or precipitates). In one embodiment, stability of a protein is measured by assaying a biophysical property of the protein, for example thermal stability, pH unfolding profile, stable removal of glycosylation, solubility, biochemical function (e.g., ability to bind to a protein (e.g., a ligand, a receptor, an antigen, etc.) or chemical moiety, etc.), and/or combinations thereof. In another embodiment, biochemical function is demonstrated by the binding affinity of an interaction. In one embodiment, a measure of protein stability is thermal stability, i.e., resistance to thermal challenge. Stability can be measured using methods known in the art and/or described herein. For example, the "Tm", also referred to as the "transition temperature" may be measured. The Tm is the temperature at which 50% of a macromolecule, e.g., binding molecule, becomes denatured, and is considered to be the standard parameter for describing the thermal stability of a protein. In another embodiment stability of a protein in a cell may be measured by determining the proteins half-life. Mutated proteins with a misfolded three dimensional structure are often targeted for degradation in the proteasome in a cell and therefore have a shorter half-life compared to the wild-type proteins.

As used herein, the term "protein function" refers to anyone of the many biochemical, cellular, physiological activities of the protein in its normal context. Such activities include, but are not limited to enzymatic catalysis, signaling, molecular binding, cellular targeting, structural functions, signaling, as well as other interactions between the protein and the many molecules in its environment, and the transformations that it undergoes or effect as a result of these interactions.

The herein disclosed invention applies for any viral infection. However, some viruses are particularly preferred, such as enveloped viruses (complex viruses), such as single and double stranded DNA and RNA viruses, and retro viruses. In some embodiments the virus infection is an infection of a single stranded RNA virus. In other embodiments the virus infection is an infection with a virus from the family of *Flaviviridae*, such as a hepatitis virus, a dengue virus or a zika virus. Specific embodiments pertain to an infection with a Hepatitis virus, such as an infection of any hepatitis virus known in the art, including but are not limited to those caused by hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV), or cryptogenic hepatitis viruses. In preferred embodiments the virus infection is a HCV infection. As used herein, the term "HCV" refers to any major HCV genotype, subtype, isolate, and/or quasispecies. HCV genotypes include, but are not limited to, genotypes 1, 2, 3, 4, 5, 6 and 7 and HCV subtypes include, but are not limited to, subtypes Ia, Ib, 2a, 2b, 2c, 3a, 4a-4f, 5 a, and 6a.

The animal of the present invention is a non-human animal, preferably a "small animal" and includes mice, rats, guinea pigs, dogs, cats, pigs, and rabbits. Embodiments of the present invention may be particularly suitable for use with small animals such as mice which will be useful as viral disease model systems for laboratory investigational studies.

The term "genetic modification" shall for the purposes of the present invention be understood in its broadest sense.

A "genetic modification" may be a stable or transient alteration of the genotype of a cell of the subject invention. The alteration may be introduced either via classical methods for mutating genomes (using mutagenic chemicals, irradiation or similar techniques) or by the intentional introduction of exogenous nucleic acids by any means known in the art (including for example, direct transmission of a polynucleotide sequence from a cell or virus particle, transmission of infective virus particles, and transmission by any known polynucleotide-bearing substance, CRISPR mediated gene editing, homologous recombination etc.) resulting in a permanent or temporary alteration of the genome to be modified. The genetic change ("modification") can be accomplished by incorporation of the new nucleic acid into the genome of the host cell, or by transient or stable maintenance of the new nucleic acid as an extrachromosomal element. The genetic modification includes within its scope knock-in and knockout genetic changes. The nucleic acids may be synthetic, or naturally derived, and may contain genes, portions of genes, or other useful polynucleotides. Methods for the alteration of genomes are well known to the skilled artisan. Also methods for the generation of genetically altered animals having a genetically modified germline are standard procedures to the skilled artisan. The term "genetic modification" or "genetically modified" shall not only pertain to modifications of a nucleotide sequence, but also include epigenetic changes. The term "epigenetic modification" refers to any modifications to genomic DNA which confer genetic information but which are not nucleotide substitutions. For example, epigenetic modifications may result from methylation of CpG DNA sequences. Methylation in a promoter region of the genome can suppress gene expression patterns.

The term "knock-in" generally refers to a heterologous or foreign polynucleotide that has been inserted into a genome through homologous recombination. The knock-in polynucleotide may be a mutant form of a gene or gene part that replaces the endogenous, wild-type gene or gene part. Such mutations include insertions of heterologous sequences, deletions, point mutations, frameshift mutations and any other mutations that may prevent, disrupt or alter normal gene expression. Thus, a "knock-in" animal, as used herein, refers to a genetically modified animal in which a heterologous or foreign polynucleotide is inserted into the genome of an animal or in which a specific gene or part thereof of an animal's genome is replaced by a foreign gene or DNA sequence. Some specific embodiments pertain to a conditional "knock-in" which includes within its scope a heterologous or foreign polynucleotide that has been inserted into a genome through homologous recombination and that elicits an activity (e.g. regulation of transcription or translation, production of a nucleotide sequence including a coding and/or non-coding sequence, etc.) at a designated developmental stage or under particular environmental conditions. A "conditional knock-in vector" is a vector including a heterologous or foreign gene or part thereof that can be inserted into a genome through homologous recombination and that can elicit an activity (e.g. , regulation of transcription or translation, production of a nucleotide sequence including a coding and/or non-coding sequence, etc.) at a designated developmental stage or under particular environmental conditions.

By "knock-out" is meant the inactivation or disruption of a gene, which decreases, abrogates or otherwise inhibits the expression, stability or functional activity of an expression product of that gene. A "knock-out" animal refers to a genetically modified animal in which a gene is disrupted. A "conditional knock-out" refers to a gene that is disrupted under specific conditions, such as a gene that is disrupted in a tissue-specific or a temporal-specific pattern. A "conditional knock-out vector" is a vector including a gene that can be disrupted under specific conditions.

A genetic modification of the invention is preferably a nucleic acid deletion, substitution, or insertion of at least one nucleic acid residue in one or more genes selected from the group consisting of CD302, Cr11, Ndufc2, AW112010, Scarb2 and Zc3hav1. The modification may either alter the structure and stability of the expressed protein, such as a frame shift producing insertion or deletion, or may be located in the regulatory sequences around the reading frame (promoter and enhancer regions) and thereby modify the expression rate of the gene. In any case specific embodiments relate to a genetic modification that disrupts the respective gene.

The terms "disruption" and "disrupted", as applied to a nucleic acid, are used interchangeably herein to refer to any genetic modification that decreases or eliminates expression and/or the functional activity of the nucleic acid or an expression product thereof For example, disruption of a gene includes within its scope any genetic modification that decreases or eliminates expression of the gene and/or the functional activity of a corresponding gene product (e.g. , mRNA and/or protein). Genetic modifications include complete or partial inactivation, suppression, deletion, interruption, blockage, or down-regulation of a nucleic acid (e.g., a gene). Illustrative genetic modifications include, but are not limited to, gene knockout, inactivation, mutation (e.g., insertion, deletion, point, or frameshift mutations that disrupt the expression or activity of the gene product), or use of inhibitory nucleic acids (e.g., inhibitory RNAs such as sense or antisense RNAs, molecules that mediate R A interference such as siRNA, shRNA, miRNA; etc), inhibitory polypeptides (e.g., antibodies, polypeptide-binding partners, dominant negative polypeptides, enzymes etc.) or any other molecule that inhibits the activity of the fertility gene or level or functional activity of an expression product of the fertility gene.

In alternative embodiments the genetic modification is not located in or in proximity of the target gene. Such modifications may be expression constructs comprising a nucleotide sequence that when expressed alter the expression, function or stability of any of the protein targets listed in the present disclosure. Most prominent examples of such an approach include transgenic RNA interference constructs comprising a nucleotide sequence targeting the expression of one or more genes selected from the group consisting of CD302, Cr11, Ndufc2, AW112010, Scarb2 and Zc3hav1. However, also the expression of dominant negative (mutated) versions of the restriction factors of the invention is possible, or constructs that when expressed induce a genome modification which then affects the expression, function or stability of a restriction factor protein of the invention. Preferred embodiments of the invention provide a genetic knock-out of one or more genes selected from the group consisting of CD302, Cr11, Ndufc2, AW112010, Scarb2 and Zc3hav1. The generation of genetic knock out animals, in particular knock out mice or rats, is well known to the skilled artisan.

"Dominant negative" refers to a gene product that adversely affects, blocks or abrogates the function of a normal, wild-type gene product when co-expressed with the wild type gene product within the same cell even when the cell is heterozygous (wild-type and dominant negative). Expression of the dominant negative mutant generally results in a decrease in normal function of the wild-type gene product.

The genetically modified animal according to the herein defined invention may in some embodiments comprise further genetic alterations which have a positive effect on viral infection. Therefore, the genome of the genetically modified animal of the invention may comprise at least one transgene for ectopic expression of the following heterologous genes, preferably human genes: Occludin (OCLN), SCARB1, CLDN1 and/or CD81.

The term "heterologous" refers to objects (e.g., nucleic acid molecules, polypeptides, cells, tissues, ere.) that do not originate from within a particular organism, tissue, or cell. For example, a "heterologous gene" refers to a gene that is not normally or naturally found in an organism or tissue of an organism.

The terms "heterologous polynucleotide", "foreign polynucleotide", "exogenous polynucleotide" and the like are used interchangeably herein to describe genetic material that has been or is about to be artificially introduced into a genome of a host organism and that is transmitted to the progeny of that host. The heterologous polynucleotide may include gene sequences found in an organism into which it is introduced or about to be introduced so long as the introduced polynucleotide contains some modification (e.g., a point mutation, the presence of a selectable marker gene, the presence of a loxP site, etc.) relative to the naturally-occurring polynucleotide. A heterologous polynucleotide may comprise a nucleic acid sequence that is capable of being transcribed into RNA and optionally, translated and/or expressed under appropriate conditions. In some embodiments, it is transcribed into a molecule that interferes with transcription or translation (e.g., antisense molecule) or mediates RNA interference (e.g., siRNA or shRNA). In some embodiments, the heterologous polynucleotide comprises a coding sequence for a peptide or polypeptide. In some embodiments, the heterologous polynucleotide comprises a targeting cassette for introducing a genetic modification into a genome.

In the event the virus for which an increased susceptibility shall be induced is a liver targeting virus such as a hepatitis virus, it may be preferred that the at least one transgene for ectopic expression of human Occludin (OCLN), human SCARB1, human CLDN1 and/or human CD81 in said genetically modified animal is expressed in the liver; for example the transgene is under expression control by a liver specific promoter such as an albumin promoter.

Additionally or alternatively, the genetically modified animal of the invention may have a reduced antiviral immune response in order to further increase the animal's susceptibility to the viral infection. The genetically modified animal could for example have a reduced expression of at least one endogenous anti-viral immune factor. As demonstrated by Dorner et al 2013 the impaired expression of at least one endogenous anti-viral immune factor selected from STAT1, IRF1, IFN-αβR and IRF7, greatly improves viral replication and spread in a non-human animal host model.

There herein disclosed genetically modified non-human animal is very useful for studying human viral diseases such as HCV infections and therefore an important new research tool for the development of therapeutics and diagnostics.

Another aspect of the invention also provides a method for the generation of a genetically modified animal as described herein before. As mentioned above, the targeted generation of genetically modified animals is well known in the art. Strategies to obtain genetically modified non-human animals according to the invention are exemplary derivable from the Dorner et al 2013 (Nature, Vol. 501) and the therein recited references.

The invention in an additional aspect also relates to the use of the genetically modified animal as described herein before in a method comprising the infection of the animal with a virus. Such a method includes for example methods for analyzing viral life cycles, or alternatively screening methods for the detection of compounds modulating viral infection. Further aspects of the invention pertain to methods comprising the infection of a herein before defined genetically modified animal with a virus, preferably a hepatitis virus. For example the invention provides a method for monitoring the a viral infection in a genetically modified animal of the invention, comprising infecting the genetically modified animal with the virus and monitoring the infection.

Yet a further aspect of the invention provides a method for enhancing or decreasing susceptibility of a cell to a viral infection, comprising reducing or increasing in the cell the expression, function and/or stability of one or more proteins selected from the group consisting of CD302, Ndufc2, AW112010, Scarb2, Cr11 and Zc3HAV1, wherein reducing in the cell the expression, function and/or stability of one or more of the proteins results in an enhanced susceptibility of the cell to the viral infection, whereas increasing in the cell the expression, function and/or stability of one or more of the proteins results in a reduced susceptibility of the cell to the viral infection.

In some preferred embodiments the method may be performed ex vivo or in vitro. In other embodiments, the method of the invention may be performed in vivo.

Preferably reducing or increasing in the cell the expression, function and/or stability of the one or more proteins is achieved by genetic modification of the cell's genome or by genetic constructs such as expression constructs or RNA interference constructs, respectively.

A cell in context of the herein described invention is preferably a mammalian cell such as a human or mouse cell. In context of a liver targeting virus, the cell is preferably a liver cell.

Further provided by the invention is a screening method for the identification of genetic factors repressing the infection of a non-human animal with human virus. The screening method of the invention comprises the steps of, a. Providing a human cell,
b. Transfecting the human cell with an expression construct for the ectopic expression of a candidate non-human animal gene in the human cell,
c. Expressing the candidate non-human animal gene in the human cell,
d. Infect the human cell from (c) with the human virus,
e. Compare the infection rate of the human cell after infection in (d) with a control, wherein a decreased infection of the human cell compared to the control indicates that the candidate non-human animal gene is a human virus infection repression factor.

The type of cell for the screening method of the invention is selected depending on the host cell spectrum of the virus to be tested. As an example, for screening repression factors of an infection with a hepatitis virus, the method ideally includes the use of a human liver derived cell.

The term "genetic factor" in context of the present invention shall refer to genes for protein expression. However, the invention may be adapted to refer to a screening method for other types of genetic factors as well, for example microRNAs. The term, "microRNA" or "miRNAs" refer to small, noncoding RNA molecules that have been found in a diverse array of eukaryotes, including plants. miRNA precursors share a characteristic secondary structure, forming short 'hairpin' RNAs. The term "miRNA" includes processed sequences as well as corresponding long primary transcripts (pri-miRNAs) and processed precursors (premiRNAs). Genetic and biochemical studies have indicated that miRNAs are processed to their mature forms by Dicer, an RNAse III family nuclease, and function through RNA-mediated interference (RNAi) and related pathways to regulate the expression of target genes (Hannon, 2002, Nature 418, 244-251; Pasquinelli, et al., 2002, Annu. Rev. Cell. Dev. Biol. 18, 495-513). miRNAs may be configured to permit experimental manipulation of gene expression in cells as synthetic silencing triggers 'short hairpin RNAs' (shRNAs) (Paddison et al., 2002, Cancer Cell 2, 17-23). Silencing by shRNAs involves the RNAi machinery and correlates with the production of small interfering RNAs (siRNAs), which are a signature of RNAi.

As used herein, the terms "RNA interference" and "RNAi" refer to a sequence-specific process by which a target molecule (e.g. , a target gene, protein or RNA) is downregulated via downregulation of expression. Without being bound to a specific mechanism, as currently understood by those of skill in the art, RNAi involves degradation of RNA molecules, e.g., mRNA molecules within a cell, catalyzed by an enzymatic, RNA-induced silencing complex (RISC). RNAi occurs in cells naturally to remove foreign RNAs (e.g., viral RNAs) triggered by dsRNA fragments cleaved from longer dsRNA which direct the degradative mechanism to other RNA sequences having closely homologous sequences. As practiced as a technology, RNAi can be initiated by human intervention to reduce or even silence the expression of target genes using either exogenously synthesized dsRNA or dsRNA transcribed in the cell (e.g., synthesized as a sequence that forms a short hairpin structure).

The rate of viral infection in the cell or population of cells may be determined by any method known in the art. In particular useful is the use of a reporter cell line as a cell of the screening method of the invention. A reporter cell line can directly produce a quantitative signal that correlates with the rate of viral infection of the cell line. The n4mBid cell line is an example of such a reporter cell line for monitoring HCV infection (Chen et al. 2010, Antiviral Research).

The non-human animal is again an animal as defined herein before.

The candidate non-human animal gene is a gene normally expressed in the liver of the non-human animal in case the screening method is applied for identifying repression factors of liver targeting viruses such as HCV.

Furthermore provided is a therapeutic method—as well as agents for use in the method—for inhibiting, mitigating or preventing viral infection of a subject, said method comprising contacting a cell in said subject with an agent which enhances virus interaction with a protein selected from the group consisting of CD302, Ndufc2, AW112010, Scarb2, Cr11 and Zc3HAV1, wherein said interaction includes any direct or indirect function of said protein repressing viral entry.

The viral interaction with the protein may be enhanced by the agent by an increased expression of the protein in said cell.

The agent for use in the therapeutic method of the invention may be selected in some embodiments from an expression construct comprising an expressible sequence which encodes a protein selected from the group consisting of CD302, Ndufc2, AW112010, Scarb2, Cr11 and Zc3HAV1.

As used herein, the terms "encode", "encoding" and the like refer to the capacity of a nucleic add to provide for another nucleic acid or a polypeptide. For example, a nucleic acid sequence is said to "encode" a polypeptide if it can be transcribed and/or translated to produce the poly-peptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

Having identified proteins which repress viral entry into host cells, a wide variety of agents are contemplated herein that support or mimic the action viral repressors of the invention. In addition to antibodies, aptamers that bind to a repressor protein of the invention can be used to inhibit viral infection. As used herein, an aptamer can comprise any DNA, RNA, oligonucleotide, or chemically modified oligonucleotide that binds to a target. Alternatively, recombinant proteins that mimic a protein selected from CD302, Ndufc2, AW112010, Scarb2, Cr11 and Zc3HAV1, or active antiviral fragments thereof, can be used to inhibit viral infection. As used herein, "recombinant proteins" are any non-naturally occurring proteins obtained by recombinant DNA or polymerase chain reaction-mediated reactions.

In practicing any of the above referenced methods involving administration of viral inhibitory, preventative or mitigating agents to a subject, it is contemplated that a variety of pharmaceutical compositions comprising these active agents can be administered by a variety of techniques. Such pharmaceutical compositions may be formulated in various ways known in the art for administration purposes. To prepare the pharmaceutical compositions of the present invention, an effective amount of the particular compound, in base or acid salt form, as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like. The pharmacologic compositions described herein may further be prepared in unitary dosage form suitable for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

A variety of in vitro and cell based assays that provide for identification of compounds or agents that enhance interactions of viruses with the repression factors of the invention are contemplated herein. Enhancing viral interactions with a protein selected from CD302, Ndufc2, AW112010, Scarb2, Cr11 and Zc3HAV1 can be used to inhibit, mitigate or prevent infection of a subject with any virus, in particular hepatitis C virus, subtype, isolate, and/or quasispecie thereof. HCV genotypes include, but are not limited to, genotypes 1, 2, 3, 4, 5 and 6 and HCV subtypes include, but are not limited to, subtypes Ia, Ib, 2a, 2b, 2c, 3a, 4a-4f, 5a and 6a. Furthermore, those skilled in the art will appreciate that agents or compounds that interact with any region of a repression protein or factor of the invention support the proteins functions that provide for the inhibition of viral entry. In vitro assays comprise any assay wherein binding, interaction or association of a recombinant repression protein with a virus such as HCV, or a component of a virus is determined. It is understood that the binding of recombinant repression proteins with a virus or components thereof can be either direct or indirect. Indirect binding would entail binding of the repression factor to the virus through an intermediary.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: cDNA library generation

FIG. 2: Library screening protocol for HCV species-specific restriction factors FIG. 3: Significant enrichment of x17 murine genes—potential restriction factors FIG. 4: Murine restriction factors do not inhibit viral replication (A) but viral entry (B).

FIG. 5: Murine repression factors inhibit viral entry for many different viral genotypes FIG. 6: Murine Cd302 & Cr11 are expressed on the cell-surface of Huh7.5 over-expressing cells FIG. 7: siRNA knock-down of repression factors FIG. 8: SiRNA knockdown rescues infectivity in Huh7.5 over-expressing cells FIG. 9: human CD302 has antiviral activity (A) but is poorly expressed (not shown); combined expression of human CD302 and human Cr11 enhances the phenotype significantly.

FIG. 10: Cd302 & Cr11 are expressed on the surface primary mouse hepatocytes FIG. 11: Infection by primary HCV from patient sera (sera 1a, 1b and 3a) is inhibited by mouse CD302 and mouse Cr11

EXAMPLES

Example 1 cDNA Library Generation (FIG. 1)

To generate a Mouse IFNα-Induced Liver Library (MIILL), a single mouse was injected with IFNα and sacrificed at 4 hrs post IFN-induction. The liver (in an antiviral state) was immediately homogenized in Trizol and total RNA extracted. The PolyA+ component of the total RNA was enriched and reverse-transcribed into cDNA. The cDNA was amplified for x15 cycles using SMART oligos containing SfiI sites (extremely rare sequence in mammalian coding DNAs). Amplified cDNA was SfiI digested and size fractionated prior to ligation into pV1 (lentiviral vector).

Example 2

Library Screening Protocol for HCV Species-specific Restriction Factors (FIG. 2)

Ligated fractions were electrorporated into ElectroMAX cells and resulting colonies sequenced to ascertain the library quality. Ligated fractions which contained high percentages of diverse full-length mouse ORFs were pooled and electroporated prior to solid phase amplication in approximately 8L medium. Prior to solid phase amplification the MIILL contained $4\times10^6$ independent clones (good coverage considering there are only $2.2\times10^4$ described mouse genes and an average tissue expresses $8\times10^3$ genes—multiple copies of each gene are contained in the library before amplification). After solid phase amplification, the pV1 MIILL was extracted from transformed bacteria using a maxiprep protocol, aliquoted and stored at −20° C. The library was packaged into VSV-G enveloped pseudoparticles (pps) using via 3-plasmid transfection into 293T cells. VSV-G, HIV-1gag/pol and pV1 MIILL plasmids were transfected in equimolar amounts using Lipofectamine 2000 and supernatents harvested at 24 h and 48 h post sodium butyrate induction. Titres of MIILLpps were calculated via TCID50 limiting dilution onto Hela-TZMbl cells. Cells were fixed and stained 72 hrs post-infection and MIILLpps aliquoted and stored at −80° C. Permissiveness of different cell-lines for MIILLpp transduction was determined via FACS.

Entry factor transgenic mice with a STAT1 knockout (4EF STAT1-/-) support only weak viral replication, indicating either a missing host factor or potent murine restriction factors. The hypothesis underlying the experimental design was that the human/murine species barrier to HCV infection is, in part, determined by murine specific restriction factors which are highly expressed in mouse hepatocytes. The inventors hypothesized that these factors may be IFN-inducible. To test this hypothesis, the inventors delivered the MIILL (1 or 2 particles per cell) to highly permissive n4mBid hepatoma cells (Kindly supplied by Charles Rice, Rockefeller). These cells are modified Huh7.5 cells which undergo programmed cell death upon HCV replication. The apoptosis cascade is started by cleavage of the Bid protein, however in n4mBid cells the cleavage site has been replaced by NS3/4A junction which is the recognition site for the HCV NS3 protease. Thus, when HCV replicates in n4mBid cells, the NS3 protease cleaves the modified Bid protein and apoptosis occurs. This was the platform on which the screen was based. First the MIILL was transduced into the n4mBid cells ($4 \times 10^6$ cells) so that every cell contained at least 1 integrated provirus encoding a murine ORF. Then iterative rounds of selection were performed with WT HCV (Jc1: MIILL2 MOI 100). Permissiveness to HCV/CoV infection was assessed using luciferase reporter viruses. After the selection experiment, a 200-fold reduction in permissiveness for HCV was observed in the cell population, which was attributable to enrichment of library delivered mouse genes which restrict HCV replication.

Example 3

Figure 3:
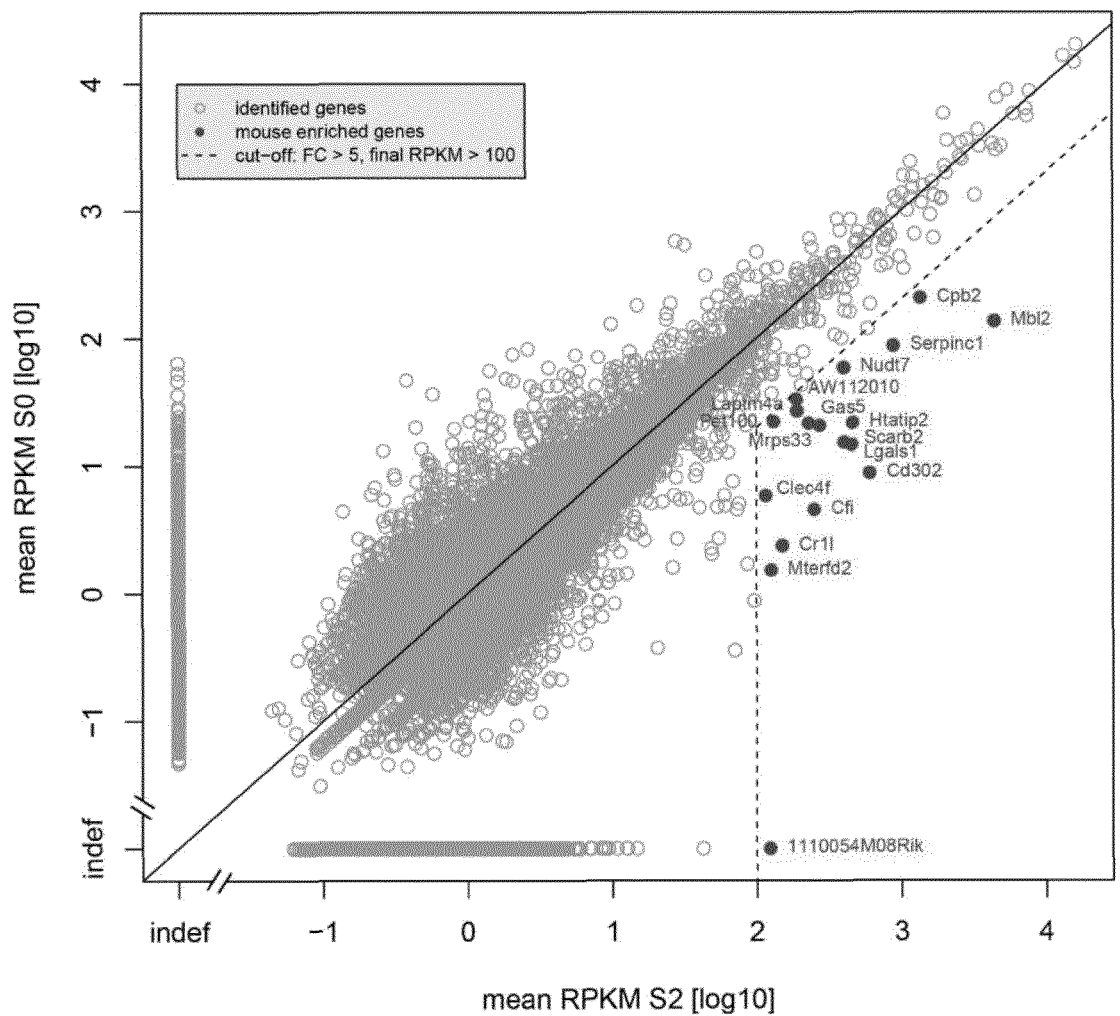

Significant Enrichment of x17 Murine Genes—Potential Restriction Factors (FIG. 3)

To identify the determinants of the reduction HCV permissiveness, RNAseq was performed on RNA extracted from transduced cells at the start of the experiment (S0) and compared with the cell population at the end of the experiment which was highly refractive for HCV infection (S2). RNAseq data was first mapped to the human transcriptome, to remove the cellular background and also to check the reduction in permissiveness was not due to depletion of an essential human co-factor over the course of the experiment (eg CD81). The remaining unmapped reads (1% of the total) were then mapped to the mouse transcriptome and represent the delivered library. The S0 mouse transcriptome was then compared to the S2 mouse transcriptome. Murine genes which were significantly enriched over the course of both experiments (FC>5; final RPKM >100) were further investigated (17 candidate genes). All transcriptomic data was analysed using CLC Genomics Workbench and individual points represent averages from 2 RNAseq technical replicates.

Example 4

Murine Restriction Factors do not Inhibit Viral Replication (FIG. 4A) but Viral Entry (FIG. 4B).

Lentiviral overexpression of individual restriction candidates in Huh7.5 cells (Kindly supplied by Charles Rice, Rockefeller) identified 3 murine genes which are potent restrictors of HCV infection (>50% reduction in permissiveness). Further characterization of Cd302 and Cr1l then commenced. (Panel A) The effect on JFH-1 subgenome replication was assessed by comparison with 2 well characterized human ISGs (NOS2 and IRF1). Subgenome replication was largely unaffected by over-expression of murine Cd302 and Cr1l. Over-expressing cells (Control, Cd302, Cr1l and Cd302/Cr1l) were infected with Jc1 R2a reporter virus (panel B). Time course infections were conducted, again using NOS2 and IRF1 as controls. Cd302 and Cr1l potently restrict infection by HCV. Over-expression of both factors simultaneously results in 2.5 log reduction in the ability to infect hepatoma cells Example 5

Figure 5:
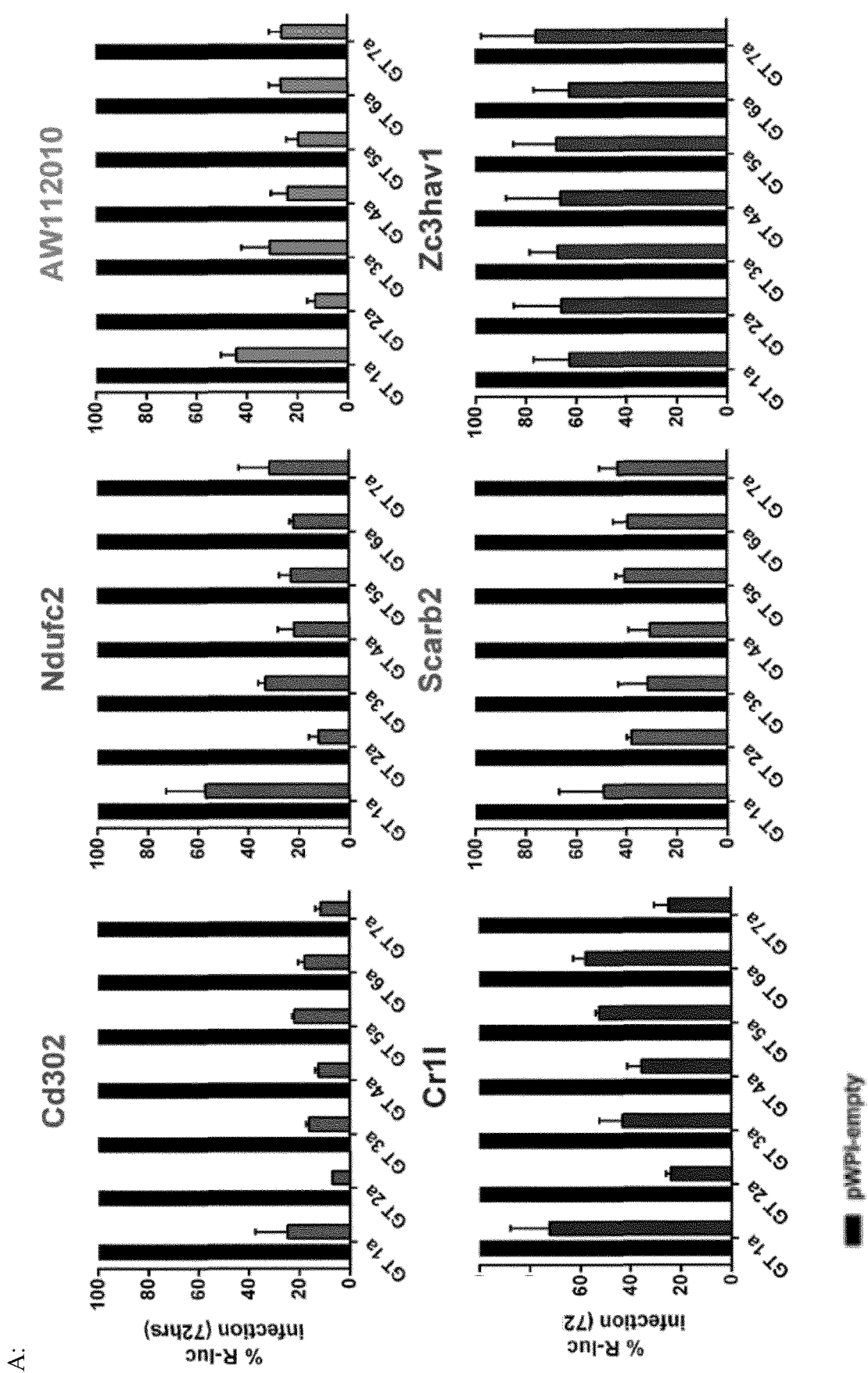
Figure 5:
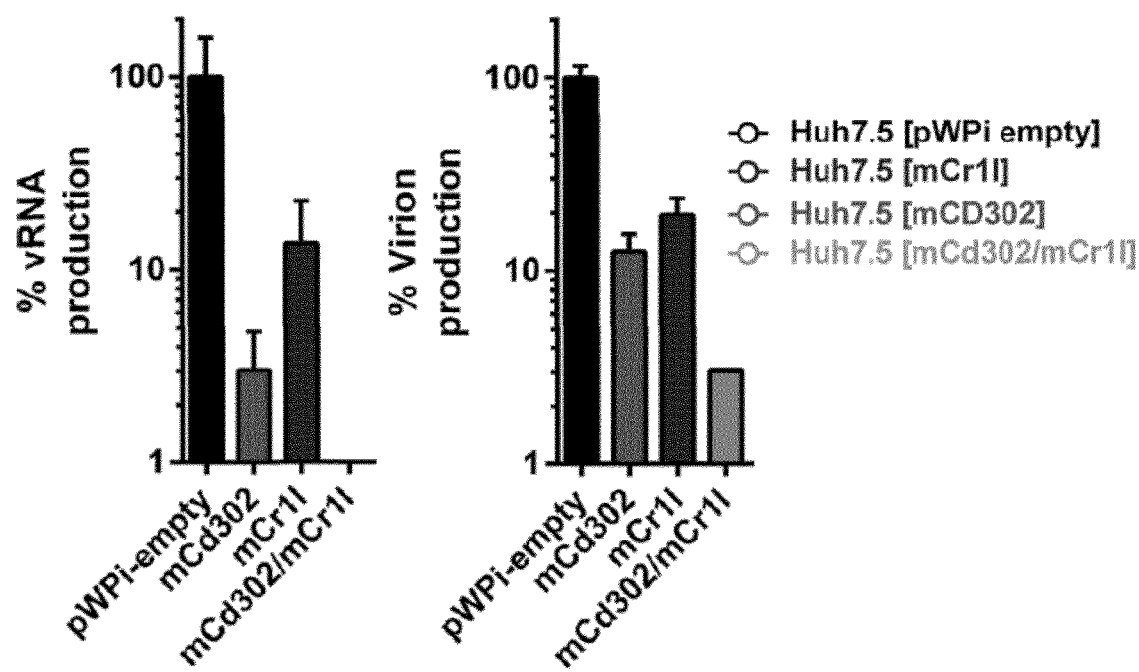

Murine Repression Factors Inhibit Viral Entry for Many Different Viral Genotypes (FIG. 5)

Over-expressing cells (Cd302, Cr1l, Ndufc2, AW112010, Scarb2 and Zc3hav1) were infected with renilla reporter viruses representing HCV genotypes 1-7 and luciferase counts measured at 72 hrs. Cells transduced with the empty vector (pWPI-empty) served as control and infection efficiency in these control cells was normalized to 100% (black bars). B: combining the disruption of multiple repression factors enhances the phenotype.

Example 6

Figure 6:
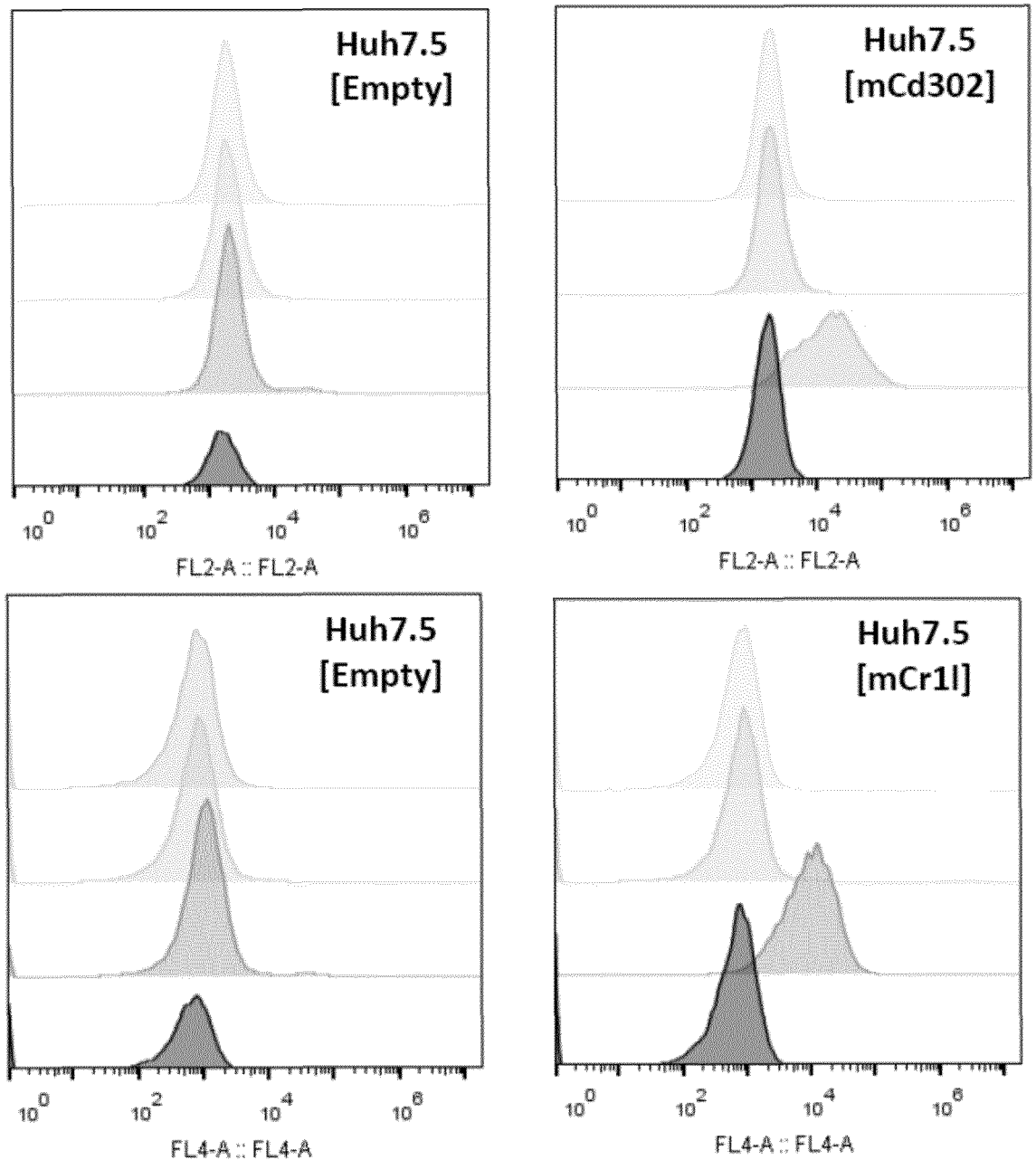

Murine Cd302 & Cr1l are Expressed on the Cell-surface of Huh7.5 Over-expressing Cells (FIG. 6)

Over-expressing cells (Control, Cd302 and Cr1l) were trypsinized. Non-permeabilized cells were stained with anti-Cd302 or anti-Cr1l antibodies, with secondary only and isotype controls also included in addition to staining of a control cell-line. Fluorescence Activated Cell Sorting (FACS) was performed and these data indicate that murine Cd302 & Cr1l are expressed on the cell-surface of Huh7.5 over-expressing cells.

Figure 7:
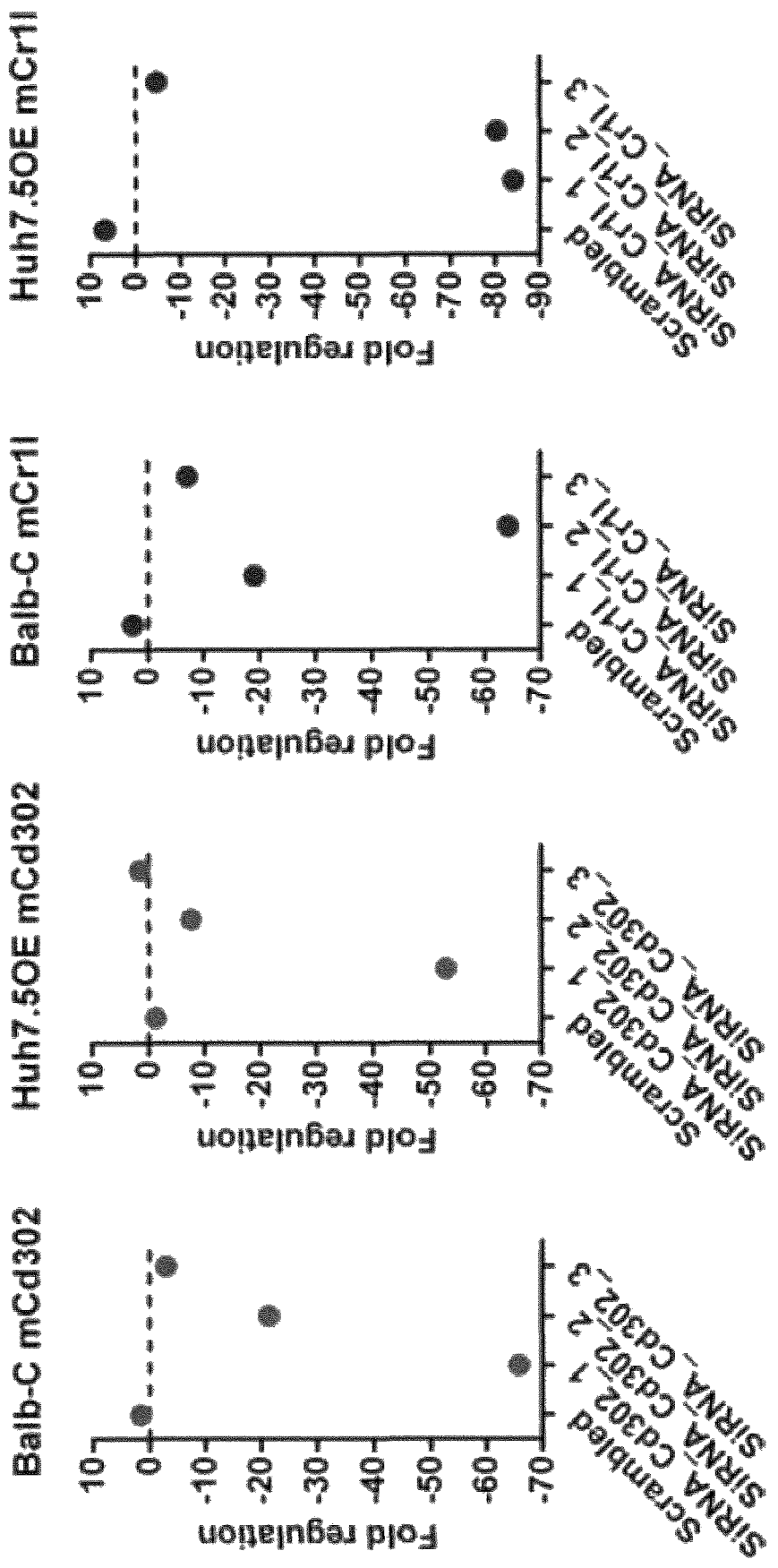

Example 7 siRNA Knock-down of Repression Factors (FIG. 7)

Characterized siRNAs were ordered from Ambion targeting either Cd302 or Cr1l. Three different siRNAs were tested for each gene in both over-expressing cells and in plated primary mouse hepatocytes. SiRNAs were transfected using Lipofectamine and incubated for 48hrs prior to RNA extraction. Knockdown of specific mRNA was then assessed by qPCR. These data revealed that Cd302_siRNA_1 and Cr1l_siRNA_2 were most effective at silencing their respective mRNAs.

Example 8

Figure 8:
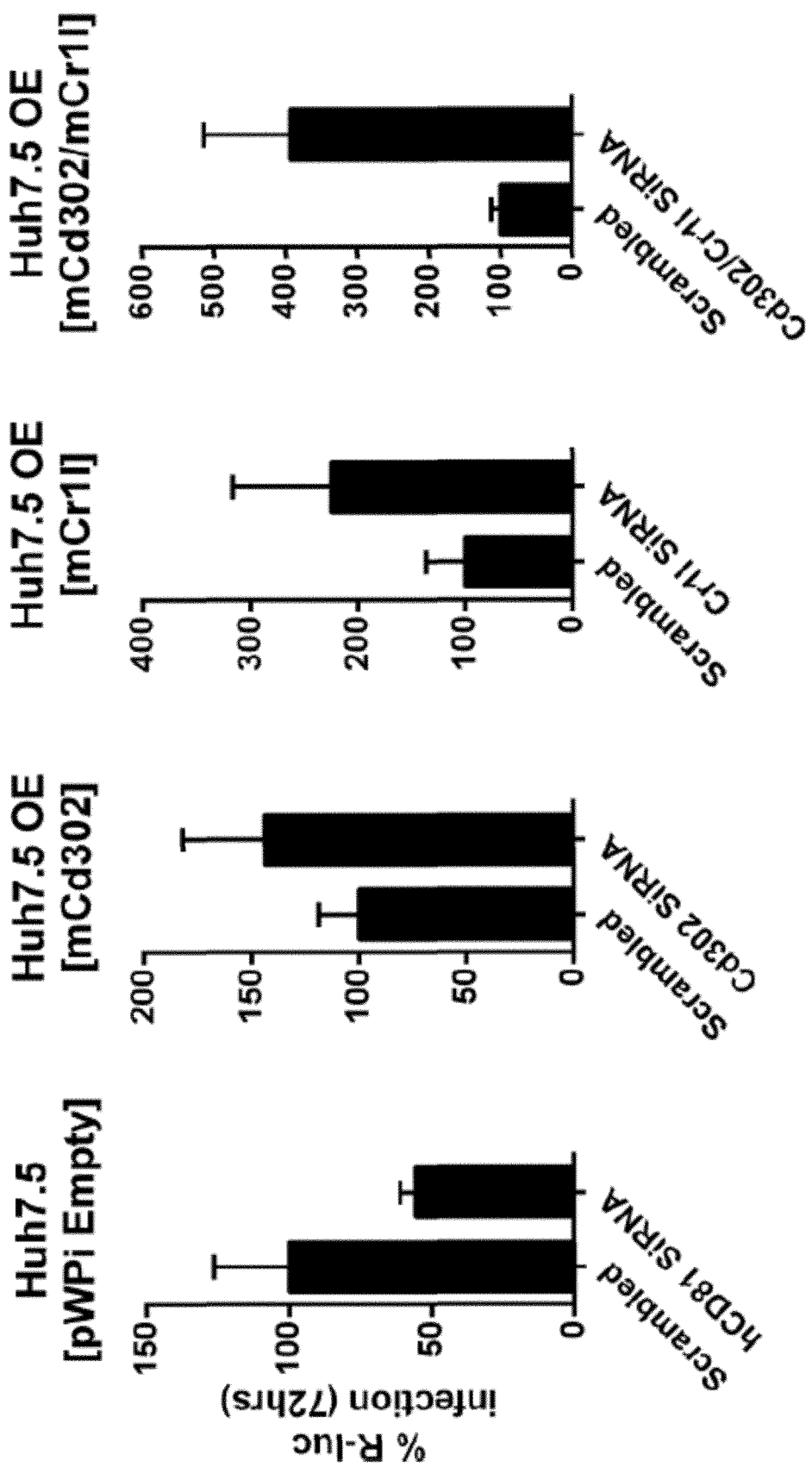

SiRNA Knockdown Rescues Infectivity in Huh7.5 Over-expressing Cells (FIG. 8)

Over-expressing cells (Control, Cd302, Cr1l and Cd302/Cr1l) were transfected with siRNAs targeting CD81, Cd302 and Cr1l or a scrambled control using Lipofectamine and incubated for 24 hrs. Transfected cells were then infected with Jc1 R2a virus and incubated for 48 hrs prior to lysis and luciferase measurement. Transfection of control cells with siRNAs targeting the viral receptor CD81 resulted in a 50% reduction in the ability to infect. Conversely, transfection of over-expressing cells with cognate siRNAs targeting Cd302, Cr1l and Cd302/Cr1l resulted in a 50% 100% and 300% increase in the ability to infect respectively.

Example 9

Human CD302 has Antiviral Activity Alone, which is Increased in Combination with Human Cr11

The human homologs of CD302 and Cr11 were tested for antiviral activity using the lentiviral over-expression system (panel A). Time course infections demonstrate the human CD302 is a potent restrictor of HCV entry while human Cr11 is not. However, a combined expression of human CD302 and Cr11 significantly increased antiviral activity (panel B). Total transcriptomic analyses of human primary hepatocytes from 3 donors indicates that human CD302 is expressed to modest levels in human hepatocytes (not shown). However, human Cr11 was expressed at a level below 1 RPKM.

Example 10

Figure 10:
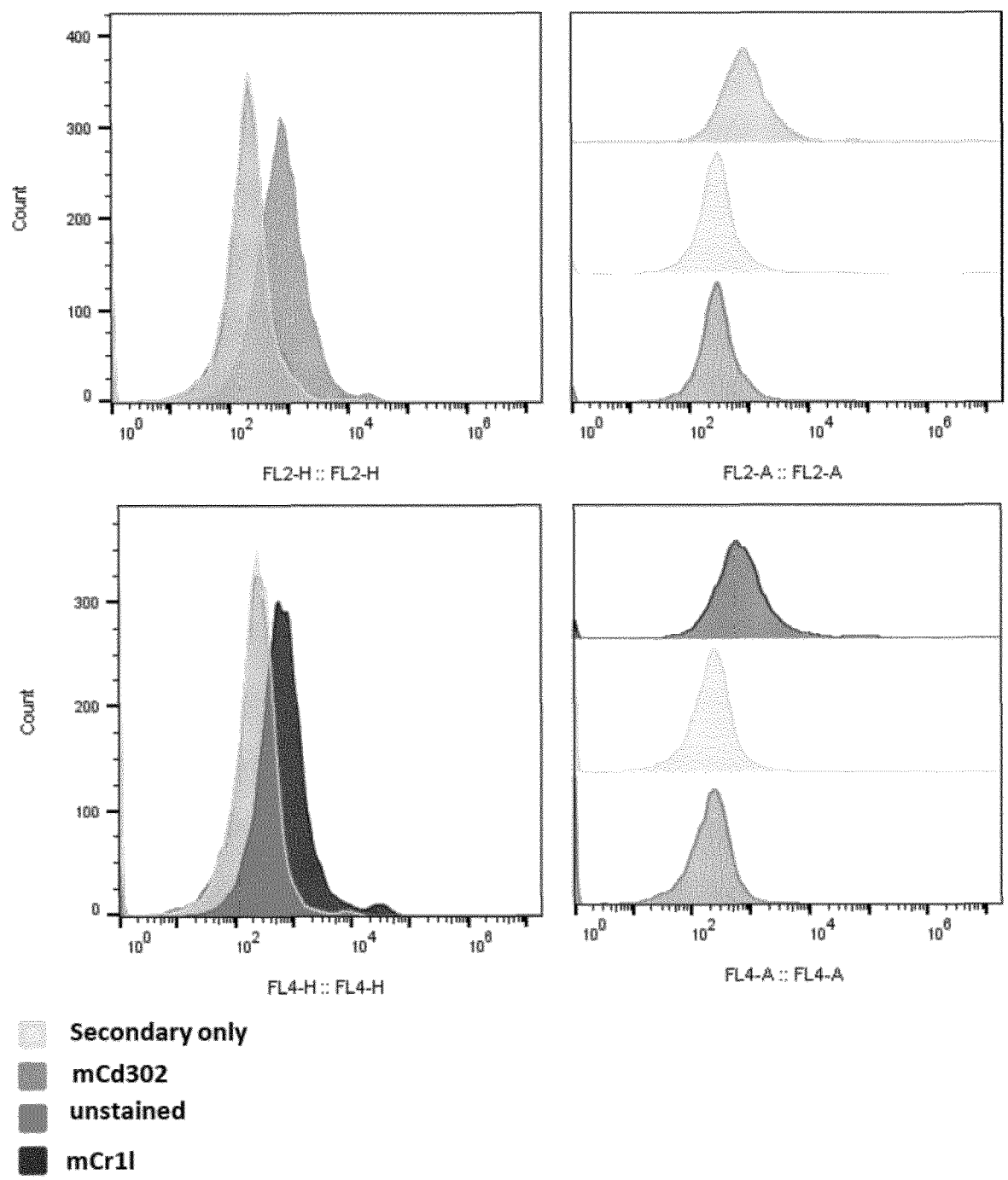
Figure 10:
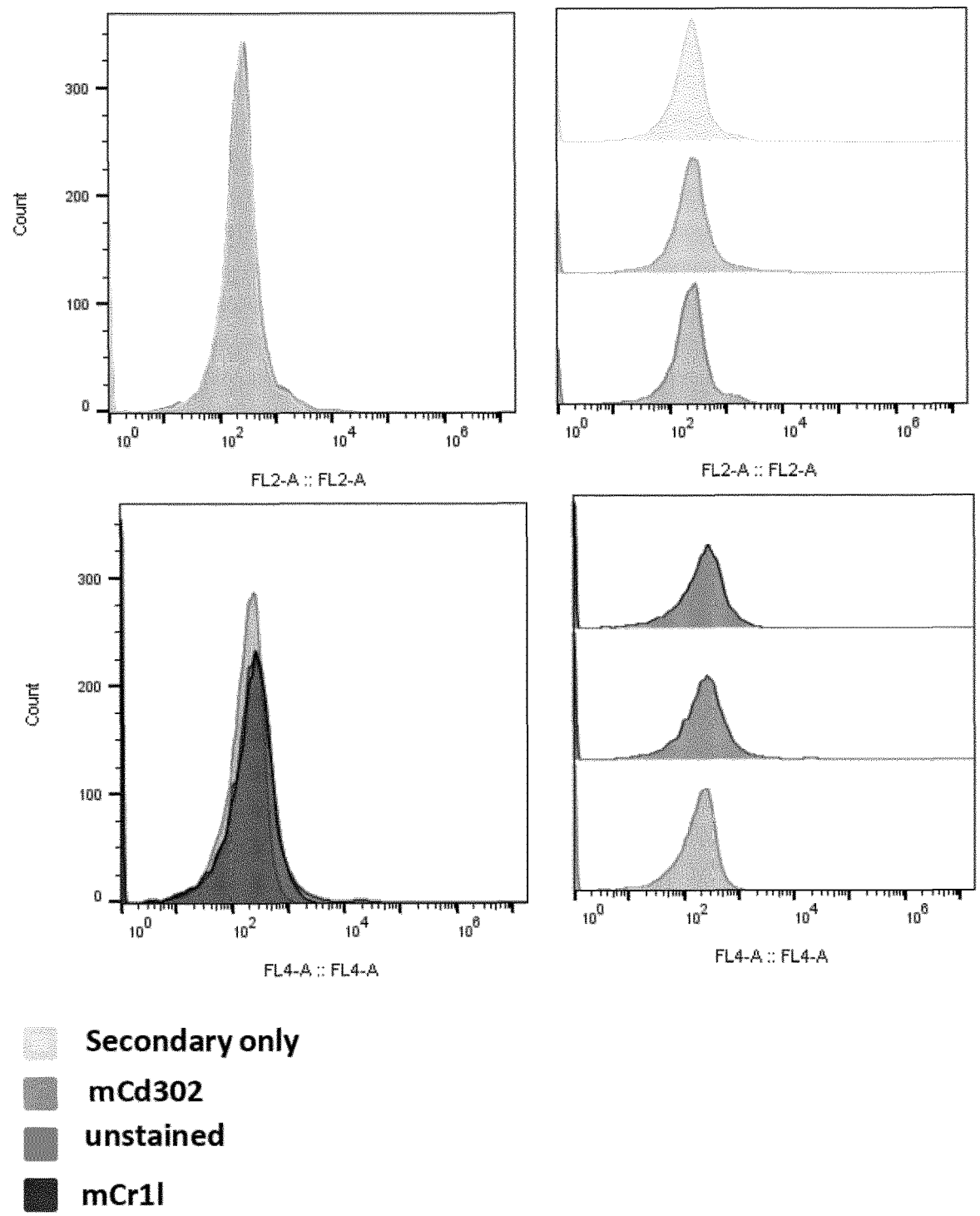
Figure 11:
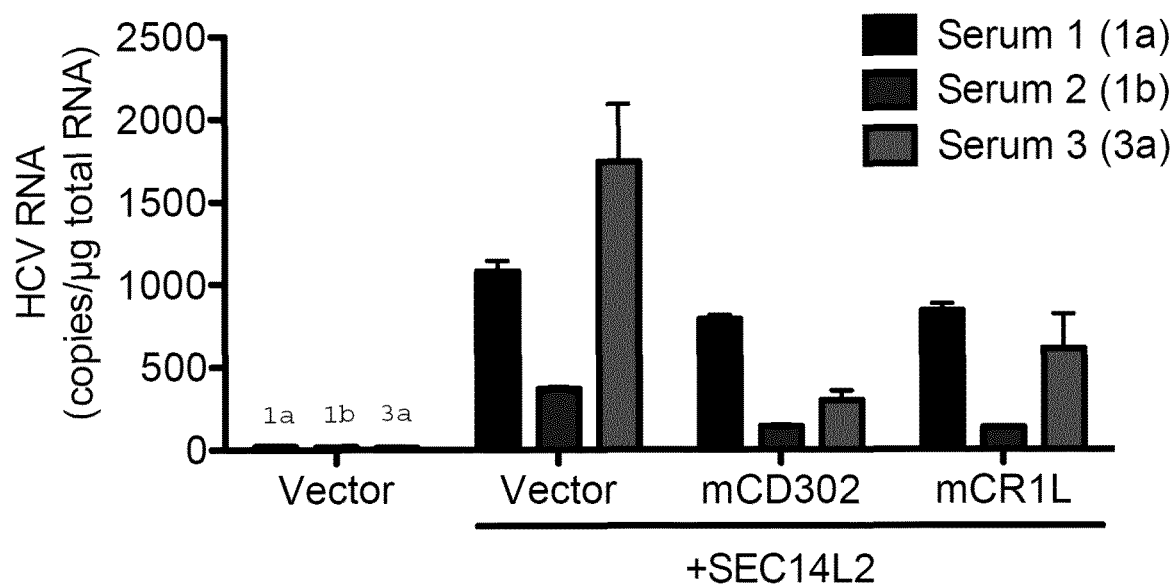

Cd302 & Cr11 are Expressed on the Surface Primary Mouse Hepatocytes (FIG. 10)

Plated primary mouse hepatocytes from an FVBN mouse were trypsinized and non-permeabilized cells were stained with anti-Cd302 or anti-Cr11 antibodies and secondary controls (panel A). Fluorescence Activated Cell Sorting (FACS) was performed and these data indicate that murine Cd302 & Cr11 are expressed on the cell-surface of mouse hepatocytes. Control Huh7.5 cells were also included with no cell surface shift observed (panel B).

Example 11

HCV from Infected Human Patient Sera is Inhibited by Murine CD302 and Cr11

Sec14L2 over-expressing Huh-7.5 cells (compare Saeed et al. 2015 Aug. 27;524(7566):471-5) were transduced with a control lentiviral, with mCD302 or with mCr11. Subsequently, these cells were inoculated with sera from patients infected with genotype 1a (black), 1b (blue) or 3a (red) viruses. Infection efficiency was quantified by RT-PCR. Virus load is decreased in mCD302 and mCR1L expressing cells indicating that these factors restrict primary, patient serum derived HCV.

The invention claimed is:

1. A genetically modified non-human animal with increased susceptibility to an infection with a hepatitis C virus, wherein the genetically modified non-human animal comprises a genome with at least one genetic modification compared to a wild-type genome of said non-human animal, characterized in that the at least one genetic modification reduces the expression, function or stability of CD302, and/or Cr11, and the genome comprising at least one transgene for ectopic expression of human Occludin (OCLN), human SCARB1, human CLDN1 and/or human CD81.

2. The genetically modified non-human animal according to claim 1, wherein the at least one genetic modification reduces the expression, function or stability of CD302 and Cr11.

3. The genetically modified non-human animal according to claim 1, which is a mouse, rat, rabbit or guinea pig.

4. The genetically modified non-human animal according to claim 1, wherein the at least one genetic modification is a mutation of at least one nucleic acid residue in the genes of CD302 and CR11.

5. The genetically modified non-human animal according to claim 1, wherein the at least one genetic modification is a dominant negative expression construct, or a transgenic RNA interference construct comprising a sequence targeting the expression of one or more genes selected from the group consisting of CD302 and Cr11.

6. The genetically modified non-human animal according to claim 1, wherein the genome comprises at least one transgene for ectopic expression of OCLN, and/or human CD81.

7. The genetically modified non-human animal according to claim 1, further having a reduced expression of at least one endogenous anti-viral immune factor.

8. A method for enhancing susceptibility of a non-human cell to an infection with a hepatitis C virus, comprising genetically modifying the non-human cell to reduce in the non-human cell the expression, function and/or stability of CD302, and/or Cr11, wherein the genetically modified non-human cell comprises a genome comprising at least one transgene for ectopic expression of human Occludin (OCLN), human SCARB1, human CLDN1 and/or human CD81.

9. The method according to claim 8, wherein said non-human cell is a mammalian cell.

10. The method, according to claim 9, wherein the mammalian cell is a mouse cell.

11. The method, according to claim 8, which is conducted in vitro.

* * * * *